United States Patent [19]
Howard

[11] Patent Number: 6,143,285
[45] Date of Patent: Nov. 7, 2000

[54] BODY POWDER COMPOSITION

[75] Inventor: John R. Howard, Ridgefield, Conn.

[73] Assignee: Combe Incorporated, White Plains, N.Y.

[21] Appl. No.: 09/338,423

[22] Filed: Jun. 23, 1999

[51] Int. Cl.[7] ............................. A61K 7/035; A61K 7/00; A61K 7/02
[52] U.S. Cl. ............................................... 424/69; 424/401
[58] Field of Search ........................................ 424/401, 69

[56] References Cited

U.S. PATENT DOCUMENTS

| 4,568,539 | 2/1986 | Ashton et al. | 424/69 |
| 4,650,670 | 3/1987 | Callingham et al. | 424/65 |
| 5,162,117 | 11/1992 | Stupak et al. | 424/475 |
| 5,858,409 | 1/1999 | Karetny et al. | 424/489 |
| 5,879,714 | 3/1999 | Sherman | 424/489 |

*Primary Examiner*—Thurman K. Page
*Assistant Examiner*—Amy E Pulliam
*Attorney, Agent, or Firm*—Fitzpatrick, Cella, Harper & Scinto

[57] ABSTRACT

A body powder composition containing croscarmellose sodium in effective moisture absorbent amounts and a powder diluent such as talc or topical starch. The composition may contain other constituents normally utilized in powders intended for topical application to the skin.

10 Claims, No Drawings

BODY POWDER COMPOSITION

BACKGROUND OF THE INVENTION

1. Field of the Invention

The present invention relates generally to powder compositions for use in human skin care. In particular, the present invention relates to a moisture-absorbing powder composition suitable for topical application to the skin comprising croscarmellose sodium.

2. Background

A number of materials, and for example, talc and topical starch, have long been used in pharmaceutical and cosmetic preparations as protective agents on skin areas exposed to excessive moisture or perspiration. Powder compositions containing talc and topical starch are used for absorbing moisture resulting from the action of the sebaceous and sweat glands. Body powders are frequently used on infants to help prevent diaper rash and otherwise help maintain dryness. Powders are also used in foot care, feminine hygiene, antiperspirants and general cosmetic products. Powders have also been incorporated into creams, ointments, solid sticks or compacts.

Talc is widely employed in skin care compositions, including powder compositions, because of its water repellent action, emollience and slip characteristics which lubricate skin surfaces. Its emollience and slip properties give talc its superior "skin feel" properties. Thus, talc is used in the formulation of cosmetics and as a powder for treating tender skin to prevent chafing and other irritation such as would occur from diapers or wet clothing. However, its ability to absorb aqueous fluids is quite limited. Compared to topical starch, which can absorb up to about 25 wt. % of aqueous fluids, talc has insignificant fluid-absorption capacity.

The advantages of combining the absorptive action of topical starch with the emollience and lubricity of talc or other skin protectant agents have been previously recognized. By way of example, Harvey (U.S. Pat. No. 4,913,896) discloses a powder that contains talc (65–80%) and starch (20–30%) together with antibacterial and/or antifungal agents. Whistler (U.S. Pat. No. 5,453,281) substitutes small granule starch for binder excipients in pills or cosmetic and/or dusting powder compositions. However, the total absorptivity (i.e., fluid-absorption capacity) of the composition is generally unsatisfactory unless substantial amounts of starch are employed. However, if the composition contains a high proportion of starch to maintain the desired absorptivity, then the beneficial attributes provided by the other agents in the composition, such as skin feel in the case of talc, are compromised.

Attempts have been made to improve the moisture absorbency properties of compositions containing talc and topical starch. For example, pregelatinized starch has been added as a minor component to talc or starch (Ashton et al., U.S. Pat. Nos. 4,485,092 and 4,568,539; Harvey, U.S. Pat. No. 4,913, 896) for the purpose of increasing moisture absorption. However, pregelatinized starch hydrates in aqueous fluids and forms a paste, thereby exhibiting a gummy character which limits the desirability of this agent for skin care formulations. Furthermore, the equilibrium moisture content (or absorptivity) of pregelatinized starch at 25° C. and 100% relative humidity is only about 40% greater than that of topical starch, which further limits the utility of this material.

Various other ingredients, including surfactants, humectants, cellulose, various polymers and the like, have been incorporated into powder compositions for the purpose of improving their skin feel. See, for example, Nichols (U.S. Pat. No. 5,209,932); Kurisaki et al. (U.S. Pat. No. 5,024, 831); and Pugh et al. (U.S. Pat. No. 4,954,334). Cellulose does not aggregate on the skin thus providing a loose sensation to the user. Furthermore, cellulose absorbs residual moisture present on the surface of the skin, resulting in an overly dry sensation to the user. Swelling and shrinking of cellulose occurs due to excess or low content of moisture in the air, respectively. Such moisture sensitivity causes cracking during or after shaping. Sodium carboxymethyl cellulose is used in a number of compositions, including a topical detergent (Birtwistle et al., U.S. Pat. No. 5,180,579), a deodorant/antiperspirant (Faryniarz et al., U.S. Pat. No. 5,135,747), dispersible tablets (Milovac et al., U.S. Pat. No. 5,047,247) and a cosmetic base (Goode et al., U.S. Pat. No. 4,946,832). Moffett (U.S. Pat. No. 3,624,200) uses talc and starch as carriers in a composition for controlling perspiration odors on human skin. Synthetic resins have also been used; however, these tend to excessively agglomerate due to their capacity to accumulate triboelectric charge. Such agglomeration causes the powder to stand out after application to the skin. The term "stand out" refers to the appearance of a powder composition after application to the skin. A composition that "stands out" is readily apparent to visual inspection: the composition may cover the skin surface so that powder-coated areas are distinguishable from non-coated areas.

Others have designed microporous cellulosic powders specifically to enhance moisture absorption in skin preparations (Nichols, U.S. Pat. No. 5,209,932). The disadvantage of such systems is that they are not usually readily available and many lack a history of safe use in humans.

Callingham (U.S. Pat. No. 4,650,670) discloses powder compositions containing certain non-cellulosic polysaccharides, including chemically modified starches and cross-linked polyvinylpyrrolidone, in order to obtain increased moisture absorbency. In particular, the non-cellulosic polysaccharides are said to be capable of absorbing an amount of moisture at least equal to their own weight.

Despite the wide variety of known body powder compositions, there is a need for a moisture-absorbing composition that overcomes the difficulties inherent in the prior art (poor skin feel, caking, agglomeration, and the like). An ideal composition for topical use should be made of safe, readily available materials, be able to disperse easily onto the skin, carry a high payload of active ingredients, have acceptable tactile properties, and be capable of absorbing a large quantity of moisture without caking or standing out on the skin.

"Super disintegrants" is a term used in the pharmaceutical industry to describe a class of readily available materials, which are widely employed in pharmaceutical dosage forms, principally in ingestible tablets and capsules. The function of these compounds is to facilitate the break-up of tablets and capsules after ingestion. Croscarmellose sodium, starch sodium glycolate and crospovidone are three common super disintegrants. (Remington: The Science and Practice of Pharmacy, 19th ed., Mack Publishing Co., vol. II, p. 1619 (1995)). Starch sodium glycolate is an insoluble low substituted carboxymethyl ether of poly-alpha-glucopyranose obtained by treatment of potato starch. Crospovidone is an insoluble cross-linked polyvinylpyrrolidone.

SUMMARY OF THE INVENTION

According to its major aspects and broadly stated, the present invention is a body powder composition containing croscarmellose sodium in effective moisture absorbent amounts and a powder diluent, such as talc and/or topical starch. The composition may also contain other constituents that are utilized in powders intended for topical application to the skin.

Other features and advantages of the present invention will be apparent to those skilled in the art from a careful reading of the Detailed Description below.

DETAILED DESCRIPTION

A body powder composition according to the present invention contains croscarmellose sodium and a powder diluent such as talc and/or topical starch. The composition may also contain other constituents normally utilized in powders intended for topical application to the skin.

As used herein, the terms "powder composition", "body powder composition" and "body powder" refer to a powder in a loose state or a pressed state, typically prepared by mixing a powder composed of a main constituent such as talc and/or topical starch with other constituents such as pigments, binders, perfumes, deodorants, and so forth.

Any suitable powder diluent may be employed in the powder compositions of the present invention. Such diluents include, without limitation, talc, starch, metal stearates, alkali or alkaline earth carbonates, alkali or alkaline earth bicarbonates, titania, zinc oxide, clays such as kaolin and mixtures thereof.

The term "talc" refers to a hydrated magnesium silicate widely used in body powder compositions. The terms "starch" and "topical starch" refer to any one of a group of carbohydrates or polysaccharides of the general composition $(C_6H_{10}O_5)_n$, occurring as organized or structural granules of varying size and markings in many plant cells.

Unless otherwise indicated, all ingredient weight % are based on the total weight of the powder composition.

Starches suitable for use in the present invention include, without limitation, cornstarch, potato starch, sago starch, rice starch, tapioca starch, and mixtures thereof; however, cornstarch is preferred since it has skin affinity, uniform natural globular particle dimensionality and purity, as well as ready availability.

To ensure an acceptable skin feel, the composition of the present invention preferably contains approximately 55 wt. %–98 wt. % of a powder diluent such as talc, more preferably approximately 80 wt. %–98 wt. % of the diluent, although greater or smaller amounts can be utilized. If greater amounts of the diluent are used, the resulting composition may not be capable of moisture absorption to the extent necessary to provide protection against wetness and irritation of the skin.

Croscarmellose sodium is an internally cross-linked form of sodium carboxymethyl cellulose, wherein cross-linking is achieved by lowering the pH during manufacture and heating. Croscarmellose sodium is fibrous in nature with a particle size of 90% $\leq 44.5$ µm and is insoluble in water. Its fibrous cross-linked structure ensures that, when water is absorbed, the integrity of the individual particles is maintained and a paste or gum does not form. Without internal cross-linking, sodium carboxymethyl cellulose forms a pasty gum on exposure to moisture, which has an unacceptable cosmetic feel.

In general, croscarmellose sodium is utilized in amounts sufficient to provide enhanced moisture absorbency upon topical application. For this and other purposes, croscarmellose sodium is preferably employed in amounts ranging from about 2 wt. % to about 20 wt. % of the total composition, more preferably from about 5 wt. % to about 20 wt. %. Amounts outside these ranges may also be utilized depending upon the desired absorbency. Importantly, improvement of water absorbency is markedly limited for compositions containing less than approximately 2 wt. % croscarmellose sodium.

Compositions containing more than about 20 wt. % croscarmellose sodium tend to assume more of the skin feel (i.e., tactile sensation) of croscarmellose sodium rather than the more acceptable skin feel of the powder diluent (talc, starch). Furthermore, at concentrations exceeding approximately 20 wt. % of the total composition, water-swollen croscarmellose sodium becomes more apparent on moist skin, rendering appearance of the applied composition less acceptable. Compositions with more than about 40 wt. % croscarmellose sodium generally exhibit a skin feel and appearance that is unacceptable to users.

For best results, sufficient croscarmellose sodium is present in the composition to absorb at least 2.5% by weight based on the total weight of the applied composition, and, more preferably, to absorb at least 20% by weight of moisture based on the total weight of the applied composition.

Other constituents normally found in body powder compositions can be added to the croscarmellose sodium-powder diluent mixture, if desired. Such constituents include, but are not limited to, flow agents, medicaments, perfumes, deodorants, disinfectants, antifungal agents, skin protectants, antibacterial agents, anti-caking agents, colorizing agents, stabilizers, antiperspirants, emollients, binders, fillers, extenders, and mixtures and dilutions thereof. Preferably, such additives are present in an amount no greater than approximately 5 wt. % of the composition. However, depending on factors such as the selection of additive(s) and the intended use of the composition, greater amounts up to about 25 wt. % of the total composition may be useful. By way of example, a composition according to the invention may contain up approximately 25 wt. % of an antifungal agent.

The constituents used in formulating the composition are preferably of a grade suitable for use in cosmetics; that is, cosmetic grade and/or pharmaceutical grade.

The resulting compositions can be used directly in powder form or compacted into cakes.

The compositions of the present invention can be prepared by any suitable technique, including mixing and blending procedures known to those skilled in the art. The powder constituents of the composition are typically mixed together, followed by the addition of liquid components (if present) through a liquid addition bar, spray device, or other suitable apparatus.

The following non-limiting examples further illustrate the present invention.

EXAMPLE 1

Compositions containing various amounts of talc, topical starch and croscarmellose sodium were prepared on a % by weight based on the total weight of the composition basis (Table 1). The components were mixed in a high shear blender to form powder compositions.

TABLE 1

| | Composition/Weight %. | | | |
|---|---|---|---|---|
| Ingredient | A | B | C | D |
| talc | 98 | 80 | — | — |
| topical starch | — | — | 98 | 80 |
| croscarmellose sodium | 2 | 20 | 2 | 20 |

EXAMPLE 2

The water absorption properties of pure talc, pure starch and the powder compositions made in Example 1 were evaluated by exposing the compositions A–D to conditions of high relative humidity and ambient temperature.

Approximately 4 grams of each powder composition was accurately weighed into a previously-weighed 3½" diameter petri dish. The dish was gently shaken to distribute the powder evenly over its surface, then reweighed to ensure that no powder was lost. The powder samples were then placed into a container, together with a small vessel of steaming water to induce a high relative humidity. The container was then sealed. It was determined that conditions of greater than 95% relative humidity were attained in the container.

The dish was removed periodically and weighed until a constant weight was achieved. The sample was returned to the sealed container after each weighing. After a constant weight was attained, the amount of moisture absorbed by the sample could be determined by subtraction of the starting weight from the ending weight as provided in Table 2.

TABLE 2

Weight change when exposed to high relative humidity.

| Composition | weight change (g) | weight change (%) |
|---|---|---|
| talc (only) | 0.0 | 0.0 |
| starch (only) | 0.7–0.8 | 17.5–20.0 |
| A | 0.2 | 5.0 |
| B | 1.0 | 25.0 |
| C | 0.8 | 20.0 |
| D | 2.1 | 52.5 |

Thus, when evaluated under the same experimental conditions as compositions A–D, talc exhibited a weight change of 0.0 grams and topical starch a weight change between approximately 0.7 and 0.8 grams (about 17.5–20.0%). As expected, the talc exhibited no propensity to absorb moisture.

The test results demonstrated that the addition of as little as 2 wt. % of croscarmellose sodium (composition A—talc only) resulted in an appreciable gain in moisture absorbency. Composition B, containing about 20 wt. % of croscarmellose sodium and talc, was capable of absorbing more moisture than topical starch alone.

Increases in moisture absorbency were also observed when the croscarmellose sodium was added to topical starch at concentrations of 2 wt. % or higher (compositions C and D). At a croscarmellose sodium concentration of 20 wt. % in topical starch, the absorbency of the composition was approximately double that achieved by 100% topical starch employed alone. In the tested compositions from about 2 to 20% croscarmellose sodium provides a moisture absorbency from 5 to 52.5% depending on the identity of the ingredients in the powder and their absorbency properties.

EXAMPLE 3

The water absorption capacity of croscarmellose sodium was further illustrated by evaluating the swelling or sedimentation volume of talc, topical starch and compositions B and D of Example 1. The swelling volume was examined using a procedure adapted from the European Pharmacopoeia, Swelling Index Test. In this procedure, 1 gram of powder was weighed into a 25 ml graduated cylinder, and 1 ml of ethanol was added to the powder. The mass was shaken to ensure that the powder was completely wetted, and then the cylinder was brought to volume with water. The cylinder was sealed and inverted every ten minutes for an hour, then allowed to stand for 30 minutes. The volume of the sediment was determined from the graduation marks on the cylinder. The readings of sediment volume were repeated every 30 minutes until two consecutive readings were the same. The higher the sedimentation volume the greater the liquid absorbency of the powder tested. The results are shown in Table 3.

TABLE 3

Sedimentation Volume.

| Composition | sedimentation volume (ml) |
|---|---|
| talc (only) | 2.2 |
| B* (talc) | 4.2 |
| topical starch (only) | 1.8 |
| D* (starch) | 2.9 |

*20 wt. % croscarmellose sodium present.

The results given in Table 3 demonstrate that the addition of croscarmellose sodium significantly enhanced the water absorption capability of standard topical powder vehicles such as talc or topical starch.

EXAMPLE 4

The skin feel of certain powder compositions was subjectively assessed by a small panel. Compositions containing talc and 20, 30, 40, 50, 60 and 80 wt. % croscarmellose sodium were prepared. In addition, pure talc, topical starch and pure croscarmellose sodium samples were evaluated. The samples were coded to prevent bias. Panelists were invited to rub the samples between the fingers and thumb to gauge the acceptability (cosmetic feel) of the powders.

Pure talc and topical starch were deemed acceptable by all panelists. In addition, all panelists found talc combined with up to 40% croscarmellose sodium to be at least minimally acceptable. However, all were able to differentiate the samples containing croscarmellose sodium in a direct comparison to pure talc. A further reduction in the concentration of croscarmellose sodium to about 20 wt. % or less resulted in an inability to reliably differentiate the composition from pure talc and such compositions were preferred. The pure (100%) croscarmellose sodium sample was found to have unacceptable tactile properties.

EXAMPLE 5

The hygroscopicity of five powder compositions was evaluated. Each of samples 1–4 contained, respectively, 98%, 93%, 88% and 78% by weight of a total weight of a mixture of sodium bicarbonate, cornstarch and talc in the same ratios and 0%, 5%, 10% and 20%, respectively, of croscarmellose sodium. The balance of the ingredients was fragrance, preservative and slip materials.

The test results demonstrated that as croscarmellose sodium replaces conventional adsorbent powder ingredients, absorbency is enhanced.

Sample 5 was commercially available Scholl's Super Absorbent Powder. Sample 5 contained cellulose, talc, aluminum chlorhydrate, salicylic acid, starch/acrylates/acrylamide copolymer and boric acid.

A standard charge (0.5 g) of each of Samples 1–5 above was exposed to a controlled high humidity environment. Each sample was weighed initially and at five subsequent time points. The hygroscopicity of each sample is as measured by weight change shown in Table 4 below:

TABLE 4

| | Hygroscopicity (% weight change) | | | | |
|---|---|---|---|---|---|
| Time (hrs) | 1‡ | 2* | 3** | 4*** | 5‡ |
| 0 | 0 | 0 | 0 | 0 | 0 |
| 4 | 3.6 | 4.3 | 4.6 | 4.7 | 3.9 |
| 24 | 13.9 | 12.5 | 14.7 | 16.1 | 14.4 |
| 48 | 21.4 | 23.9 | 26.0 | 25.5 | 19.0 |
| 72 | 28.6 | 32.9 | 36.0 | 33.8 | 21.7 |
| 96 | 37.3 | 42.3 | 46.6 | 48.8 | 23.5 |

‡0 wt. % croscarmellose sodium.
*5 wt. % croscarmellose sodium.
**10 wt. % croscarmellose sodium.
***20 wt. % croscarmellose sodium.

EXAMPLE 6

The same five powder Samples 1–5 tested in Example 5 were tested for total water absorption capacity. A known weight of each of the powders was suspended in about 25 ml water. The mix was shaken and then allowed to stand for 30 minutes. At the end of this period, the solids were filtered from the mix under vacuum until there was no visible surface liquid. The sample was then reweighed and the absorption calculated on a weight basis (compensating for the soluble material that is part of the powder composition). The results are shown in Table 5 below.

TABLE 5

| Total water absorption capacity. | |
|---|---|
| Sample | total water absorption capacity (%) |
| 1‡ | 34.9 |
| 2* | 80.1 |
| 3** | 117 |
| 4*** | 209 |
| 5‡ | 13.4 |

‡0 wt. % croscarmellose sodium.
*5 wt. % croscarmellose sodium.
**10 wt. % croscarmellose sodium.
***20 wt. % croscarmellose sodium.

The results show that where from 5 to 20 wt. % croscarmellose sodium was substituted for corresponding amounts of the primary active ingredients that total water absorption capacity increased 2.5 to 6 times.

Comparative Example 1

Two powder compositions are prepared containing (A) talc, topical starch, sodium bicarbonate and 10% croscarmellose sodium and (B) talc, topical starch, sodium bicarbonate and 10% sodium carboxymethyl cellulose, wherein the talc, topical starch, and sodium bicarbonate are present in the same amounts in (A) and (B). The compositions are exposed to a high relative humidity environment as in Example 2. Composition (A) of the present invention swells, but otherwise maintains its integrity and does not form a paste or gum, while Composition (B) forms a pasty gum, which has an unacceptable cosmetic feel.

It will be apparent to those skilled in the art that many changes and substitutions can be made to the preferred embodiments herein described without departing from the spirit and scope of the present invention as defined by the following claims.

What is claimed is:

1. A body powder composition comprising:
    croscarmellose sodium in an amount sufficient to provide effective moisture absorbency upon topical application; and
    a powder diluent selected from the group consisting essentially of talc, topical starch, and mixtures thereof.

2. The composition according to claim 1, wherein said composition contains at least about 2 wt. % of croscarmellose sodium based on the total weight of said body powder composition.

3. The composition according to claim 1, wherein said composition contains no more than about 20 wt. % croscarmellose sodium based on the total weight of said body powder composition.

4. The composition according to claim 1, wherein said powder diluent is cosmetic grade talc or pharmaceutical grade talc.

5. The composition according to claim 1, wherein said powder diluent is a starch selected from the group consisting of corn starch, rice starch, potato starch, sago starch, tapioca starch, modified starch, and mixtures thereof.

6. The composition according to claim 1, further comprising at least one constituent selected from the group consisting of flow agents, medicaments, perfumes, deodorants, disinfectants, antifungal agents, skin protectants, antibacterial agents, anti-caking agents, colonizing agents, stabilizers, surfactants, antiperspirants, mildew-proofing agents, emollients, alcohols, binders, extenders, fillers, antioxidants, ultraviolet absorbers, and mixtures thereof.

7. The composition according to claim 6, wherein said composition contains no more than about 25 wt. % of said at least one constituent based on the total weight of said body powder composition.

8. A method for controlling body moisture comprising:
    topically applying a body powder composition, wherein said body powder composition comprises croscarmellose sodium in an amount sufficient to provide effective moisture absorbency and a powder diluent selected from the group consisting essentially of talc, topical starch, and mixtures thereof.

9. The method according to claim 8, wherein from about 2 wt. % to about 20 wt. % croscarmellose sodium is present in said body powder composition.

10. A body powder composition comprising:
    (a) croscarmellose sodium in an amount from about 2 to 20% based on the total weight of said body powder composition to provide effective moisture absorbency and acceptable skin feel without formation of paste or gum residue upon topical application; and
    (b) a powder diluent selected from the group consisting essentially of talc, topical starch, and mixtures therefore.

* * * * *

UNITED STATES PATENT AND TRADEMARK OFFICE
CERTIFICATE OF CORRECTION

PATENT NO. : 6,143,285
DATED : November 7, 2000
INVENTOR(S) : John R. Howard

It is certified that error appears in the above-identified patent and that said Letters Patent is hereby corrected as shown below:

<u>Column 8,</u>
Line 64, "fore." should read -- of. --.

Signed and Sealed this

Twenty-third Day of October, 2001

Attest:

*Nicholas P. Godici*

NICHOLAS P. GODICI
*Attesting Officer*     *Acting Director of the United States Patent and Trademark Office*